(12) United States Patent
Liu et al.

(10) Patent No.: US 8,675,193 B2
(45) Date of Patent: Mar. 18, 2014

(54) NEAR-FIELD MATERIAL PROCESSING SYSTEM

(76) Inventors: Jian Liu, Sunnyvale, CA (US); Huan Huang, Fremont, CA (US)

( * ) Notice: Subject to any disclaimer, the term of this patent is extended or adjusted under 35 U.S.C. 154(b) by 183 days.

(21) Appl. No.: 13/454,042

(22) Filed: Apr. 23, 2012

(65) Prior Publication Data

US 2013/0278930 A1     Oct. 24, 2013

(51) Int. Cl.
    *G01J 3/30*     (2006.01)

(52) U.S. Cl.
    USPC .......................................................... 356/318

(58) Field of Classification Search
    USPC ......................................... 356/300, 317, 318
    See application file for complete search history.

(56) References Cited

U.S. PATENT DOCUMENTS

2007/0008045 A1 *    1/2007    Camparo et al. ............. 331/94.1

* cited by examiner

*Primary Examiner* — Tarifur Chowdhury
*Assistant Examiner* — Abdullahi Nur
(74) *Attorney, Agent, or Firm* — Taboada Law Firm, PLLC; John M. Taboada

(57) ABSTRACT

Methods and systems for real time feedback and control of near-field material processing are disclosed, including generating electromagnetic radiation from a USP laser coupled to a central processing unit; coupling the electromagnetic radiation to an acousto-optic modulator; coupling the electromagnetic radiation to a beam delivery system; coupling the electromagnetic radiation to a beam delivery fiber; using the electromagnetic radiation to generate a plasma on a target mounted to an adjustable stage coupled to the central processing unit; coupling the electromagnetic radiation from the plasma to a plasma spectrum collection system; coupling the electromagnetic radiation to a spectrum analysis unit; coupling the electromagnetic radiation to a detector; coupling the detector to the central processing unit; wherein the central processing unit uses the output from the detector as feedback in making adjustments to the USP laser and the adjustable stage. Other embodiments are described and claimed.

36 Claims, 14 Drawing Sheets

NEAR-FIELD MATERIAL PROCESSING SYSTEM

I. BACKGROUND

The invention relates generally to the field of laser material processing using ultra-short pulsed laser with nanometer precision. The laser material processing system has active real time control and optimization for material processing. More particularly, the invention relates to a near-field assisted, laser material processing system with nanometer resolution and plasma spectrum feedback for real time control and characterization.

II. SUMMARY

In one respect, disclosed is a system comprising: a central processing unit; a USP laser; an acousto-optic modulator comprising an input and an output, wherein the USP laser is coupled to the input of the acousto-optic modulator; a beam delivery system comprising an input and an output, wherein the output of the acousto-optic modulator is coupled to the input of the beam delivery system; a beam delivery fiber comprising an input and an output, wherein the output of the beam delivery system is coupled to the input of the beam delivery fiber and the output of the beam delivery fiber is configured to emit a laser pulse; an adjustable stage coupled to the central processing unit and configured to allow positioning of a sample at the output of the beam delivery fiber; a plasma spectrum collection system comprising an input and an output, wherein the input of the plasma spectrum collection system is positioned to allow coupling of a plasma electromagnetic radiation generated on the sample by the laser pulse; a spectrum analysis unit comprising an input and an output, wherein the output of the plasma spectrum collection is coupled to the input of the spectrum analysis unit; and a detector comprising an input and an output, wherein the input of the detector is coupled to the output of the spectrum analysis unit and the output of the detector is coupled to the central processing unit.

In another respect, disclosed is a system comprising: a central processing unit; a USP laser; an acousto-optic modulator comprising an input and an output, wherein the USP laser is coupled to the input of the acousto-optic modulator; a beam delivery system comprising an input and an output, wherein the output of the acousto-optic modulator is coupled to the input of the beam delivery system and the output of the beam delivery system is configured to emit a laser pulse; an adjustable stage coupled to the central processing unit and configured to allow positioning of a sample at the output of the beam delivery system; a plasma spectrum collection system comprising an input and an output, wherein the input of the plasma spectrum collection system is positioned to allow coupling of a plasma electromagnetic radiation generated on the sample by the laser pulse; a spectrum analysis unit comprising an input and an output, wherein the output of the plasma spectrum collection is coupled to the input of the spectrum analysis unit; and a detector comprising an input and an output, wherein the input of the detector is coupled to the output of the spectrum analysis unit and the output of the detector is coupled to the central processing unit.

In another respect, disclosed is a method for real time feedback and control of near-field material processing, the method comprising: generating electromagnetic radiation from a USP laser coupled to a central processing unit; coupling the electromagnetic radiation from the USP laser to an input of an acousto-optic modulator; coupling the electromagnetic radiation from an output of the acousto-optic modulator to an input of a beam delivery system; coupling the electromagnetic radiation from an output of the beam delivery system to an input of a beam delivery fiber; using the electromagnetic radiation from an output of the beam delivery fiber to generate a plasma on a target mounted to an adjustable stage coupled to the central processing unit; coupling the electromagnetic radiation from the plasma to an input of a plasma spectrum collection system; coupling the electromagnetic radiation from an output of the plasma spectrum collection system to an input of a spectrum analysis unit; coupling the electromagnetic radiation from an output of the spectrum analysis unit to an input of a detector; and coupling an output of the detector to the central processing unit; wherein the central processing unit uses the output from the detector as feedback in making adjustments to the USP laser and the adjustable stage.

In yet another respect, disclosed is a method for real time feedback and control of near-field material processing, the method comprising: generating electromagnetic radiation from a USP laser coupled to a central processing unit; coupling the electromagnetic radiation from the USP laser to an input of an acousto-optic modulator; coupling the electromagnetic radiation from an output of the acousto-optic modulator to an input of a beam delivery system; using the electromagnetic radiation from an output of the beam delivery system to generate a plasma on a target mounted to an adjustable stage coupled to the central processing unit; coupling the electromagnetic radiation from the plasma to an input of a plasma spectrum collection system; coupling the electromagnetic radiation from an output of the plasma spectrum collection system to an input of a spectrum analysis unit; coupling the electromagnetic radiation from an output of the spectrum analysis unit to an input of a detector; and coupling an output of the detector to the central processing unit; wherein the central processing unit uses the output from the detector as feedback in making adjustments to the USP laser and the adjustable stage.

Numerous additional embodiments are also possible.

III. BRIEF DESCRIPTION OF THE DRAWINGS

Other objects and advantages of the invention may become apparent upon reading the detailed description and upon reference to the accompanying drawings.

Figure 1:
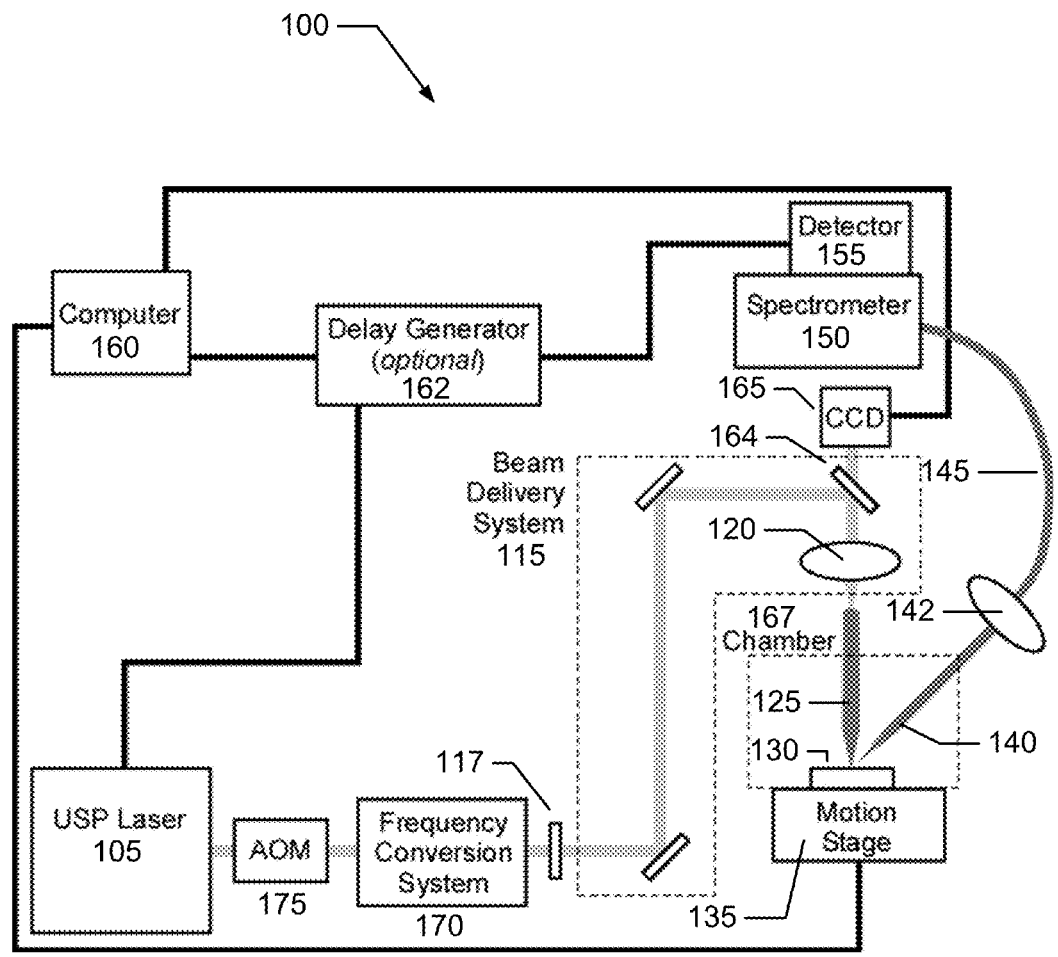
FIG. 1 is a schematic diagram of a near-field material processing system with real time feedback and control, in accordance with some embodiments.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

IV. DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

Lasers have been used to remove or otherwise manipulate materials in a variety of ways. Practical applications of laser processing commonly use pulsed laser, and more commonly use short pulsed laser. More recently, ultra-short pulsed (USP) lasers have been employed for laser processing or machining The use of USP lasers has significantly improved the machining efficiency and precision. USP lasers are capable of quickly removing material due to their extremely high intensity energies which results in the instantaneous increase of the material temperature into a plasma regime. USP lasers are more effective in overcoming common thermal damage problems associated with traditional lasers. However, current laser processing techniques offer micron-level materials processing and no real time characterization of the processing results or control. A nano-level, laser material processing apparatus and technique would be desirable. Such an apparatus has several end uses, such as modifying the refractive index of material, surface or sub-surface marking, welding, hole drilling, material cutting, thin film scribing and thin layer removing or deposition.

There exist several techniques for nano-level processing. One such technique, nano-patterning requires both high resolution (small feature size) and high throughput (number of features fabricated per time). Two dimensional patterning such as optical lithography and nano-imprinting are capable of achieving both high resolution and high throughput. However, both methods have drawbacks for direct adoption for fabrication of a wide variety, small scale, and flexible production of photonics devices. Optical lithography has a higher equipment cost as well as longer mask fabrication lead times. Nano-imprinting has the problem of overlay defects, template patterning, and template wear.

Other techniques for nano-level processing are point-to-point writing or scanning-probe based techniques such as atomic force microscope lithography and dip-pen lithography. These techniques are flexible and relatively inexpensive, but they are not without drawbacks. One of the main drawbacks of this approach is their limited throughput due to the fundamental nature of the point by point writing strategy. Throughput may be enhanced by utilizing a parallelized-tip approach. However, such mechanical point-by-point writing methods have serious issues in parallelization of the probes.

Nano-level processing may also be accomplished by laser nanofabrication. Laser nanofabrication has become increasingly important due to the rapid development of nanophotonics, super-resolution optical lithography, ultrahigh density optical data storage, and biomedical devices. Using USP laser pulses in laser nanofabrication has the unique feature of deterministic damage threshold due to the short pulse duration. In laser nanofabrication, the minimum achievable structure size is determined by the diffraction limit and is on the order of the laser wavelength. In the case where the laser focus is in the far-field zone of the focusing elements, the optical diffraction limit imposes that light cannot be confined to a lateral dimension smaller than roughly one half of the wavelength in free space. One of the solutions to this limitation is to use near-field techniques. In the near-field, evanescent waves dominate over free waves in the vicinity of scattering objects and thus, sub-diffraction-limited focus (as small as ~10 nm) can be achieved. Near-field optics is a branch of optics that considers configurations that depend on the passage of light to, from, through, or near an object with sub-wavelength features and the coupling of that light to a second object located a sub-wavelength distance from the first object. A strong, local optical field is established in the sub-wavelength region between the two objects, usually between nano-aperture and substrates. Due to the intensity field enhancement in the near-field region, the optical power on the substrate surface can exceed the ablation threshold of the substrate material and nano features can be generated. By lowering the ablation threshold of the substrate material with direct irradiation, the feature size fabricated by this technique can be smaller than the half size of the incident light wavelength. In this invention, nano-level processing is accomplished by using near-field enhancement to achieve laser material processing with nanometer precision. Near-field enhancement may be achieved through the use of a nano-tip or nano-aperture.

In order to realize ultra high precision with laser material processing, it is necessary to integrate the laser processing with high precision, real time monitoring of the process parameters and high precision, real time characterizing of the processed results. Integrated system control can provide real time manipulation of the laser parameters and performance relative to different processing times and locations. By coordinating plasma spectrum collection, analysis, and system control, it is possible to adjust laser performance in order to counteract relatively long term variations associated with processing environment conditions, sample-to-sample variations, and location-to-location variations. For example, the laser processing system can change the pulse overlap rate (pulse repetition rate over sample moving speed) and the pulse energy for different material type during processing.

The system can further allow control of the laser wavelength for material processing via the optical conversion system.

Laser-Induced Breakdown Spectroscopy (LIBS) is a type of atomic emission spectroscopy using highly energetic laser generated plasma to ablate and excite a solid, liquid, or gaseous sample. LIBS has been shown to be a powerful sensor technology in detecting and discriminating chemical hazards, biological hazards, explosive hazards, radionuclide hazardous materials both in close-contact and standoff modes. As a versatile method, LIBS has the primary advantages of versatile sampling, rapid analysis, little or no sample preparation, sensitive to a wide variety of elements, simultaneous analysis of multi-elements, and small amounts of material, and practically non-destructive. LIBS utilizes a focused high power laser onto a small area of the sample surface to vaporize and excite the sample in one step. In the LIBS technique, a pulsed laser beam is typically focused at a test point to produce a spark. The spark in the focal region, generates high density plasma with temperatures in excess of 10,000 K. At the high temperatures during the early plasma, the ablated material breaks all chemical bonds and dissociates into excited ionic and atomic species. During this time, the plasma emits a continuum of radiation which does not contain any specific wavelengths depending on the elements. As the plasma cools, the electron density of the plasma decreases and the continuum emission fades, such that each elemental emission line has a particular optimum in particular plasma and the characteristic emission are clear enough to detect elements. This optimum depends on the time/temperature history of the plasma, which in turn is dependent on the laser pulse energy and pulse length.

When the laser pulse is on the order of nanoseconds, a significant amount of the later part of the energy pulse goes into heating the plasma formed during the earlier part of the pulse through linear absorption. The plasma formed is very highly ionized which results in large amounts of continuum emission, especially at short time scales. The air molecules also contribute to the broad emission background observed in the LIBS spectrum when nanosecond laser pulses are used to produce the breakdown. To avoid the difficulties of the broad emission background when using nanosecond pulsed lasers of the prior art, the broad continuum must be given time to decay before the desired spectra of the species for analysis are detected. This, however, has the disadvantage of limiting the use of the LIBS method when attempting to detect ion species at low concentrations and is an additional source of error in the measurement. Use of a gated detector to reduce background emission and thus, improve the signal to noise ratio and minimize spectral interferences between species may be used. Another disadvantage of LIBS processes with long pulsed nanosecond laser is the phenomenon of temperature dependent bleaching and large heat-affected zone as a result of linear absorption of the laser energy. The methods of the invention described herein take advantage of the unique effects of USP lasers. When USP laser pulses are tightly focused onto the surface of materials, the high intensity inside the focal volume due to the tight focusing of the short laser pulse will induce multi-photon or tunneling ionization and subsequent avalanche ionization occurs. This nonlinear absorption results in the creation of hot plasma and subsequent heating to the surrounding materials. Because the ultrashort laser pulses of the present invention have lower energies than nanosecond pulses, less damage to surrounding materials and less ablation of material being analyzed by the laser spark occurs. Furthermore, less energy is transmitted to the air and surrounding materials. However, since nanosecond laser pulses are not conducive to submicron spatial resolution owing to the imparted thermal diffusion length, use of USP laser is beneficial for improving spatial resolution and providing sufficient momentum for collision dominated breakdown process, and therefore improved LIBS signal to background emission ratio. Therefore, USP lasers provide a LIBS process with an improved sensitivity, signal to background emission ratio, and spatial resolution.

The embodiment or embodiments described herein may solve these shortcomings as well as others by proposing a novel near-field material processing system with real time feedback and control. The laser material processing system utilizes a USP laser with near-field enhancement to achieve nanometer resolution. Feedback is provided during laser ablation or processing and is used to control the process parameters.

FIG. 1 is a schematic diagram of a near-field material processing system with real time feedback and control, in accordance with some embodiments.

In some embodiments, the material processing system 100 comprises a USP laser source 105. Next, an acousto-optic modulator (AOM) 175 is used to adjust the repetition rate of the output laser pulses. The laser output from the acousto-optic modulator 175 is coupled to a beam delivery system 115. An attenuator 117 may be used to attenuate the laser pulses prior to coupling into the beam delivery system 115. The beam delivery system 115, delivers the collimated laser output to a coupler 120 such as an objective lens where the laser output is coupled to the input of a beam delivery fiber 125. The output of the beam delivery fiber 125 has a nano-aperture. In the embodiment where a nano-tip is used, the beam delivery fiber 125 is not used and instead the output from beam delivery system is focused directly onto the sample surface to create a plasma at the point where the nano-tip is positioned over the sample. The rest of the description, minus the beam delivery fiber, applies to both the nano-aperture and nano-tip embodiments.

A sample fixture 130 secures the sample to be processed at the output end of the beam delivery fiber 125. The sample fixture 130 is mounted to a multi-axis motion stage 135 to allow for accurate positioning of the sample. In this embodiment the multi-axis motion stage is capable of being adjusted in the X, Y and Z axis. Other stages with additional adjustability in theta (rotation about the X or Y-axis) and phi (rotation about the Z-axis) are possible for adjustability in five axis of motion. The laser pulses from the beam delivery fiber 125 create a plasma on the surface of the sample. The plasma comprises excited ionic, atomic, and molecular species of the ablated surface of the sample. The electromagnetic information from the plasma plume is collected with a plasma spectrum collection system. The plasma spectrum collection system comprises a tapered optical fiber 140 that couples, with a coupler 142, the electromagnetic information from the plasma plume into an optical fiber bundle 145. The tapered optical fiber 140 may be oriented in any position in order to maximize the coupling of the electromagnetic information. The opposite end of the optical fiber bundle 145 is coupled to a spectrum analysis unit such a spectrometer 150 where a grating within the spectrometer 150 disperses the electromagnetic information from the plasma plume. The spectrometer 150 can be a monochromator, a spectrograph, or a polychromator. The spectral range of the spectrometer 150 may be chosen to suit different applications. In some embodiments, the spectral range can be a few tens of nm for observing a specific portion of the wavelength range. Alternatively, the spectral range can be from UV to NIR. A detector 155 is used to detect the grating dispersed electromagnetic information and to feed this information to a central processing unit or computer 160. The detector 155 provides increased resolution and greater selectivity of the spectral information. The detector 155 may optionally comprise an intensified charge-coupled device (ICCD) or a micro-channel image intensifier plate. The intensifier plate is preferably gated during a period of time when the plume emits characteristic optical emission. This period coincides with an optimum plume luminance period. This period follows emission of continuum radiation. Continuum radiation lacks useful specific species or elemental information. In one embodiment, a delay generator 162 may be included to provide gating of the detector to allow temporal resolution of the detector response time. Alternative embodiments of the detector can include a detector other than an ICCD, for example a suitable CCD or a suitable photomultiplier. The computer 160 may include a control system for providing synchronization of the USP laser source 105, the detector 155, and the multi-axis motion stage 135. The computer 160 may include a display for displaying spectral information and motion stage position information as well as application software and database information with known sample materials processing standard spectrum for different processing conditions in order to achieve real time analysis of the elemental composition of the sample. In some embodiments, the beam delivery system includes a dichroic mirror 164 for allowing the viewing of the target via a CCD camera 165 or other optical imaging device. The camera 165 may be used ahead of or behind the pulse to sense the location of the prospective machining path or to check the machining quality. Connecting the camera 165 to the computer 160 provides another feedback for the total overall control of the material processing system. The material processing system may include a system frame for housing all the various components described herein. The system frame may include an air filtered chamber 167 capable of removing the debris and contaminants produced during the material processing.

In some embodiments, a frequency conversion system 170 may be utilized to extend the wavelengths at which the sample is processed and analyzed with. The different probe wavelengths may lead to different LIBS signals, thus expanding the utility of the material processing system by being able to change the spot size, focus position, wavelength, pulse energy, pulse width and/or repetition rate quickly as the laser ablation switches from material to material and layer to layer.

The term "ultra-short pulse laser" or "USP laser" refers to a laser beam generated in the form of extremely brief and finite intervals, i.e., pulses. USP lasers used herein are characterized by various parameters. For instance, "pulse duration" refers to the length of time of each interval wherein the laser beam is generated. A suitable pulse duration may be, e.g., between about 1 fs to about 50 ps, preferably between about 100 fs to about 10 ps. The parameter "pulse energy" refers to the amount of energy concentrated in each interval wherein the laser beam is generated. Pulse energy may be between about 0.001 µJ to about 100 mJ, more preferably between about 0.01 µJ to about 1 mJ. The single pulse fluence refers to the pulse energy delivered over the focal spot size. It may be between 0.001 $J/cm^2$ to 100 $J/cm^2$, preferably between about 0.1 $J/cm^2$ to about 10 $J/cm^2$. The parameter "repetition rate" refers to the number of pulses that are emitted per second, and indirectly relates to the time between each pulse emission, i.e., the length of time between each pulse. The repetition rate may be between about 1 kHz and about 100 MHz, preferably between about 100 kHz and about 10 MHz. The USP laser beam of the invention may be of any wavelength in the electromagnetic spectrum from deep UV to IR range. The wavelength may be between about 100 nm to about 10 µm, more preferably between about 100 nm to about 5 µm.

The material processing system of FIG. 1 may be applied in material processing, including fabrication of micro-electro-mechanical systems (MEMS). Fabrication of MEMS demands comparable processing of various layers and structures made of different materials, including metals, ceramic, plastics, semiconductors, glasses, tissues (soft and hard), etc. Many devices are made of layered thin film structures with a plurality of interconnected functional layers that are conductive, semi conductive, insulating, doped, or protective. In particular, the ultra-short pulse duration and near-field enhanced intensity makes it possible to produce extremely high target intensities with relatively low pulse energy. The high target intensities, in conjunction with ultra-short pulse duration, enable precise micron/nano-level materials processing with minimal and/or manageable heat transfer to the target substrate per pulse.

Figure 2:
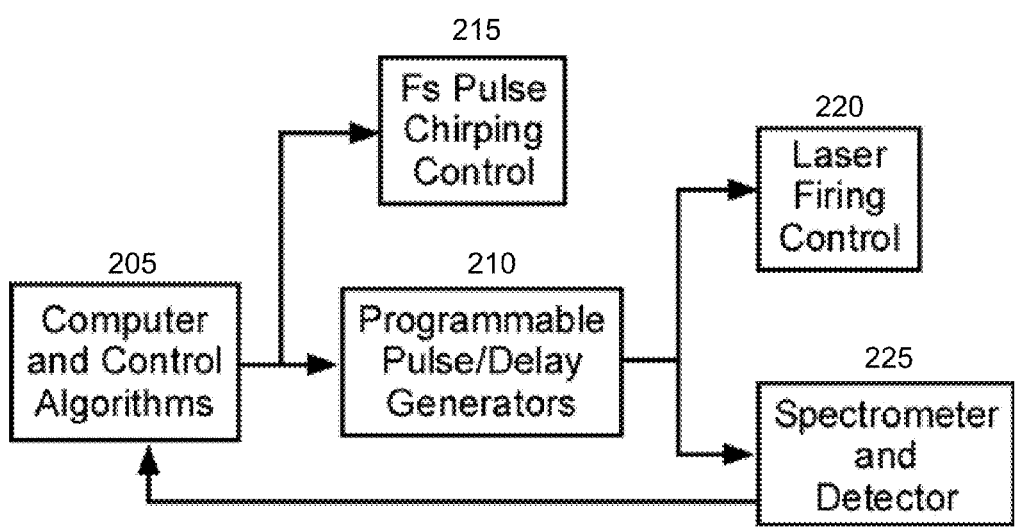
FIG. 2 is a schematic illustration of the synchronization and control system design, in accordance with some embodiments.

FIG. 2 is a schematic illustration of the synchronization and control system design, in accordance with some embodiments.

In some embodiments, the synchronization and control system will be coordinated by the system processor computer 205 through a delay/pulse generator 210 and associated electronics. The delay/pulse generator has a resolution of 5 ps and four output channels which are used to control the pulse firing time and sequence 215 of the USP laser 220, as well as the gate time of the detector and the spectrometer integration time 225. The delay is optional based on the requirement of the spectrum signal level and the signal-to-noise ratio.

Figure 3:
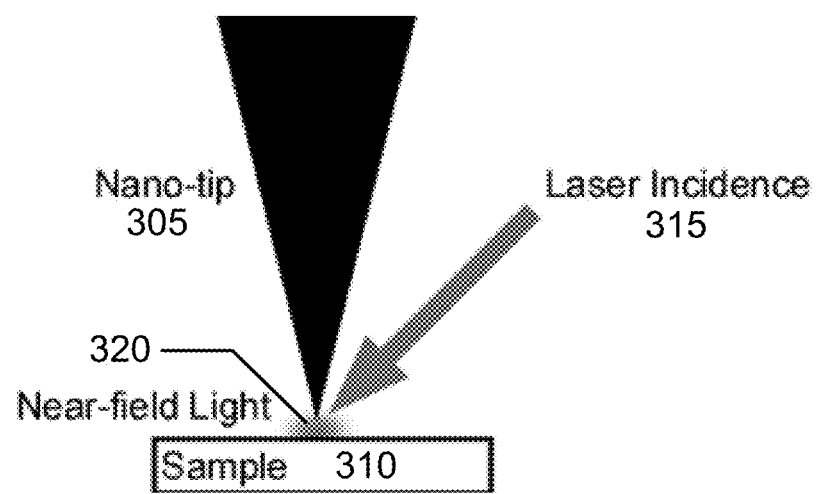
FIG. 3 is an illustration of a nano-tip for near-field enhancement generation, in accordance with some embodiments.
Figure 4:
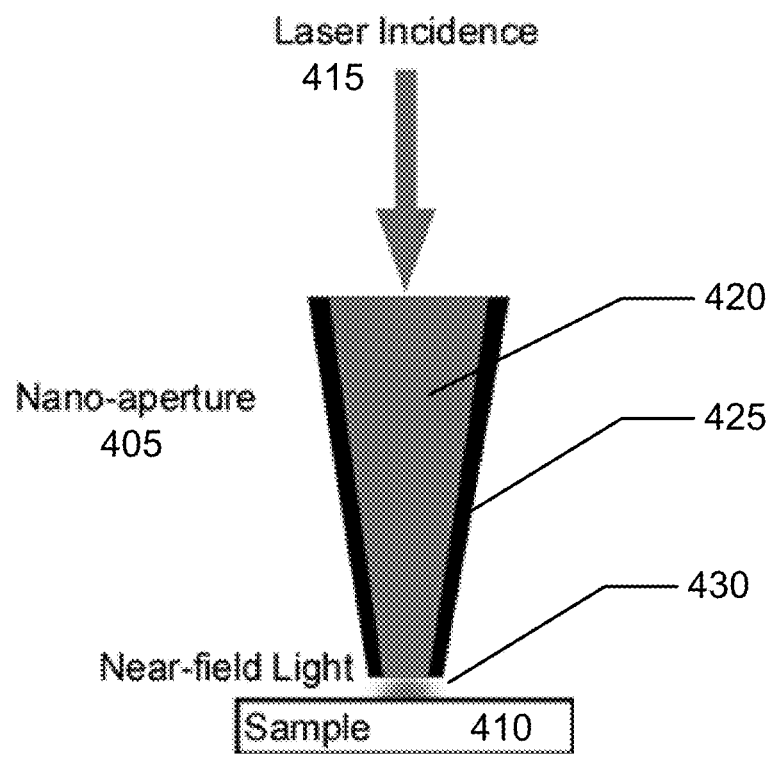
FIG. 4 is an illustration of a nano-aperture for near-field enhancement generation, in accordance with some embodiments.

FIG. 3 and FIG. 4 are illustrations of a nano-tip and a nano-aperture for near-field enhancement generation, in accordance with some embodiments.

In some embodiments, the near-field material processing system uses either a nano-tip or nano-aperture for lowering the energy threshold to create a plasma. The USP laser delivers the laser pulses required to create sparks on the surface of the sample and another optical fiber collects the emission signals from the spark. Using a nano-aperture allows the creation of a compact source probe. The fabricated source/probe is coated on the fiber surface to confine the scattering at the tip. The tip or aperture of the probe is in the nanometer range. Using a fine scanning platform, the fiber probe and the sample are brought together within a controlled distance using feedback based on response. To process the material, the sample is raster scanned with the probe held stationary in its lateral position. FIG. 3 shows a nano-tip 305 within nanometer range of the sample 310. When the laser pulses 315 from the USP laser incident from the side of the nano-tip 305 hit the surface of the sample 310, a plasma or spark 320 is created between the nano-tip 305 and the sample 310. Using the nano-tip reduces the threshold energy required to create the plasma. The plasma can then be analyzed by the spectrometer of the system to provide composition information about the sample. FIG. 4 shows a nano-aperture 405 within nanometer range of the sample 410. In contrast to the nano-tip, the laser pulses 415 from the USP laser are guided through the nano-aperature 405. The nano-aperture 405 comprises a tapered fiber 420 with a metal coating 425 to confine the scattering at the tip of the nano-aperture 405. The laser pulses 415 hitting the surface of the sample create a plasma 430 that can be analyzed by the spectrometer of the system.

In some embodiments, different apertures or tip shapes and sizes will be used. The nano-tip or nano-aperture shapes can be square, circular, "C" shape, tapered structure, donut shape or triangular shape, etc. General methods for optical fiber tip fabrication include thermal pulling, etching techniques, focused ion beam milling, laser micro-machining, etc. Near field enhancement results of a typical C-aperture nano-aperture, have all the advantages described above to construct a flexible, inexpensive high resolution and high throughput nano-patterning apparatus. The latest breakthrough overcomes the problems with previous optical structures which have similar mechanical and dimensional issues for highly integrated arrayed approaches, such as bow-tie apertures, namely that there are two near-field spots, one each for each tip, and the difficulties in supporting them in a dense parallel structure. In addition, the nano-aperture enables a background free writing, which is crucial for nano-patterning by using photo resist, as opposed to the bow-tie or other nano-antenna structures. The new nano-apertures are capable of high resolution patterning of a high aspect ratio structure, which is essential to extend this technology for 3 dimensional (3D) nano-patterning. The key operation principle is separating the functions of intensity enhancement for an effective usage of photons of excitation laser and spatial confinement of a single tapered antenna, so that manufacturing process can be optimized to increase yield, and improve reliability.

Figure 5:
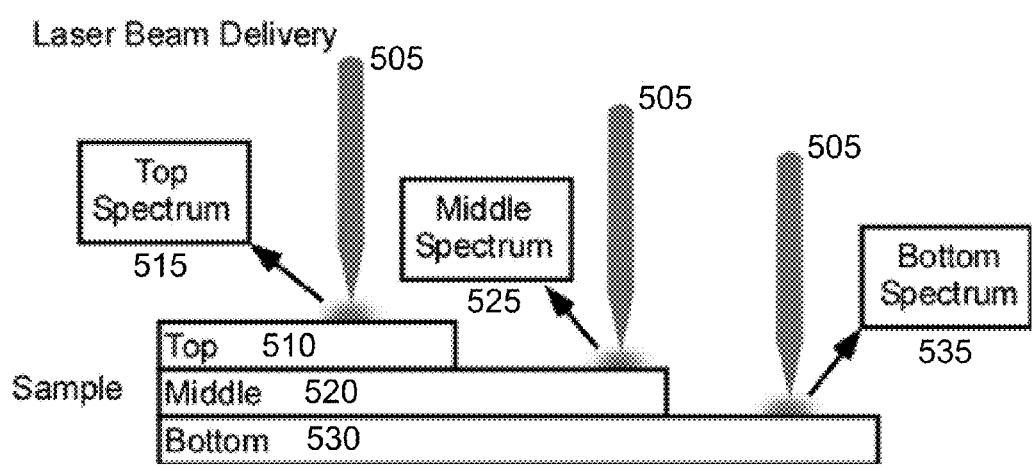
FIG. 5 is a schematic illustration of laser material processing across a structure comprising three different material layers resulting in three different plasma spectrum signals, in accordance with some embodiments.

FIG. 5 is a schematic illustration of laser material processing across a structure comprising three different material layers resulting in three different plasma spectrum signals, in accordance with some embodiments.

In some embodiments, the near-field material processing system may be used on a structure that comprises two or more different material layers. When the laser pulses 505 hit the top layer 510, a plasma with the primary chemical elements of the ablated material of the top layer 510 will be created. The plasma results in a plasma spectrum signal of the top layer 515. Eventually the laser pulses 505 will reach the middle layer 520 resulting in a plasma with the primary chemical elements of the ablated material of the middle layer 520. The plasma results in a plasma spectrum signal of the middle layer 525 and by analyzing the differences in the spectrum signal, the laser processing parameters may be adjusted based on the material type. The ablation process may continue to the bottom layer 530 where another plasma with the primary chemical elements of the ablated material of the bottom layer 530 is created. The plasma results in a plasma spectrum signal of the bottom layer 535. The system is capable of determining when the bottom layer is reached by looking for any change in the plasma spectrum signal between the layers.

Figure 6:
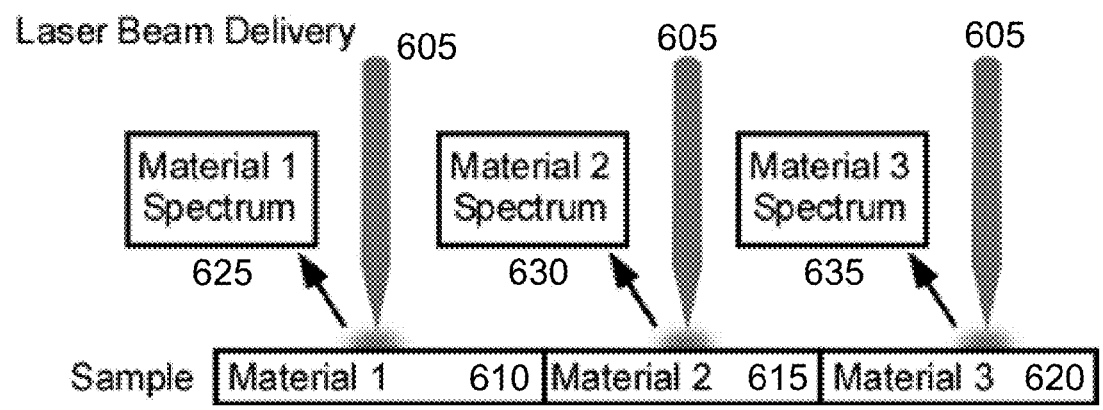
FIG. 6 is a schematic illustration of laser material processing across a one-layer structure comprising three different materials resulting in three different plasma spectrum signals, in accordance with some embodiments.

FIG. 6 is a schematic illustration of laser material processing across a one-layer structure comprising three different materials resulting in three different plasma spectrum signals, in accordance with some embodiments.

In some embodiments, the near-field material processing system may be used on a single layer sample that comprises two or more different materials. The laser pulses 605 will create plasmas with different plasma spectrum signals depending on the material of the sample. For a sample with three different material composition, 610, 615, 620, the laser pulses 605 will result in plasmas with three different plasma spectrum signals 625, 630, 635. Optical spectrum analysis identifies that the primary chemical elements of the ablated material are different and it will then be reported to the system control. The system determines that the change is referring to the change of new material and so relative laser processing parameters will be adjusted based on the material composition of the sample. This analysis potential makes it possible to repair and analyze why a device failed. To accomplish this, typically a plastic encapsulation layer needs to be removed. With the material processing system of FIG. 1, the USP laser pulses may be scanned in a two-dimensional pattern across the plastic encapsulation surface to ablate the plastic encapsulation layer from the device. During the ablation process, the system is capable of distinguishing between the plastic and the underlying integrated circuit. The material processing system of FIG. 1 can monitor the status of the target substrate and confirm/control the focal position relative to the surface of the target substrate.

Figure 7:
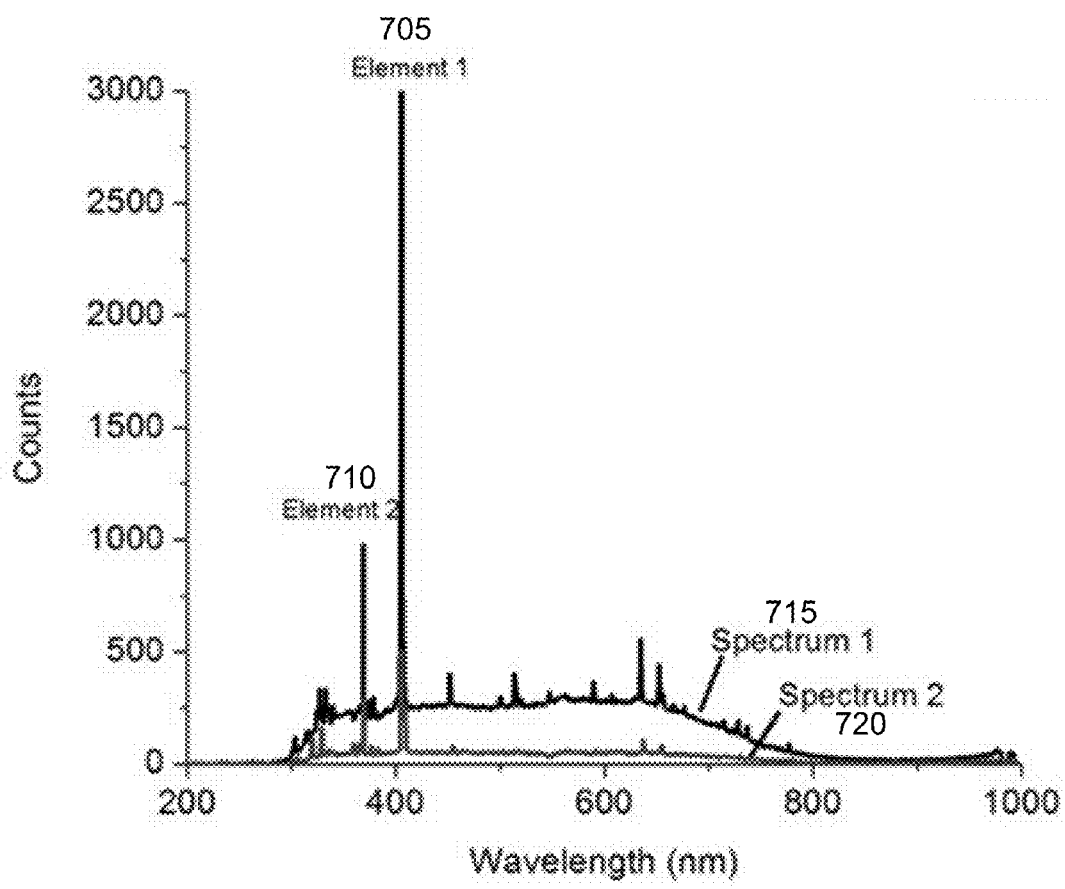
FIG. 7 is a graph showing two spectrographs of the same material with different laser processing conditions, in accordance with some embodiments.

FIG. 7 is a graph showing two spectrographs of the same material with different laser processing conditions, in accordance with some embodiments.

In some embodiments, different processing conditions are used on the same sample material. FIG. 7 illustrates a comparison of two spectrographs for the same material but with different processing conditions. The spikes correspond to different elemental features. The relative counts (amplitude) of the spectrum spikes are different for example for the spikes of Element 1, 705, and Element 2, 710. The amplitudes of the spikes represent specific writing conditions, including pulse energies, specific pulse overlap rates, or any combinations. In FIG. 7, for example, Spectrum 1, 715, with higher counts (amplitude) corresponds to a higher scanning speed and Spectrum 2, 720, with lower counts (amplitude) corresponds to a lower scanning speed. Monitoring the counts thus provides a way of monitoring the scanning speed processing conditions. This provides the feedback to the system for the processing conditions and processing qualities. A change of counts reflects the change of processing conditions.

Figure 8:
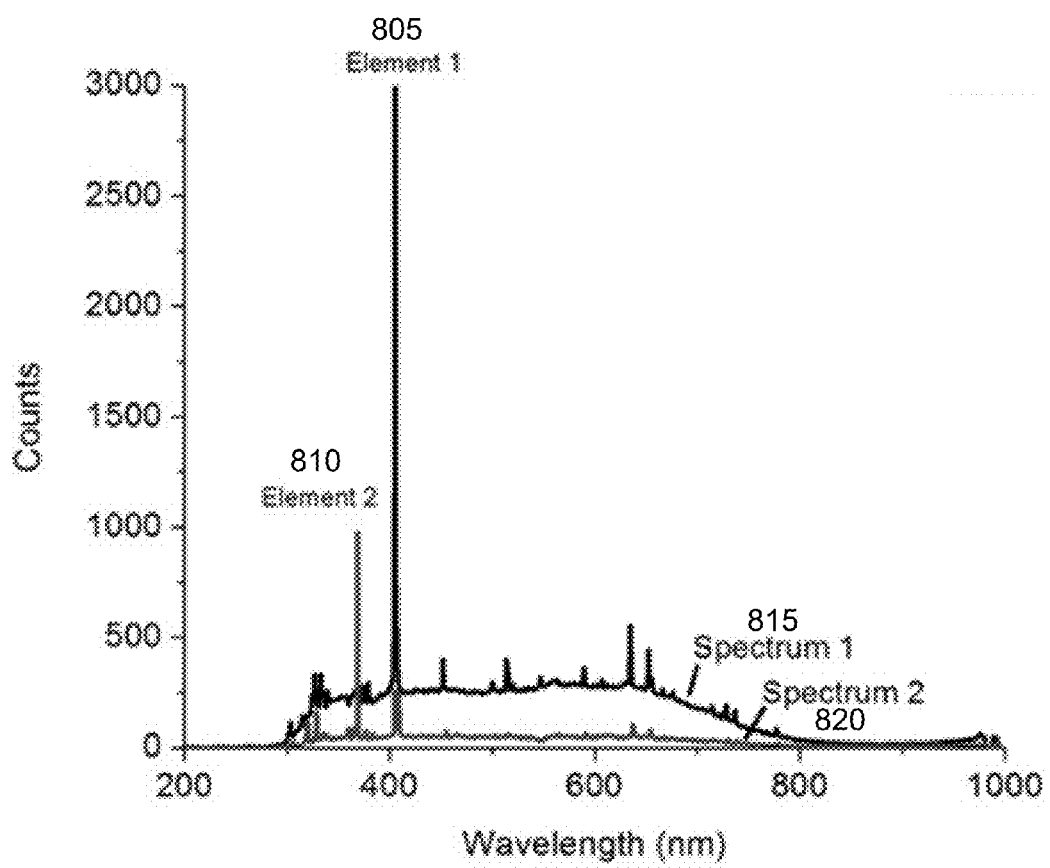
FIG. 8 is a graph showing two spectrographs of material with different element concentrations with the same laser processing conditions, in accordance with some embodiments.

FIG. 8 is a graph showing two spectrographs of material with different element concentrations with the same laser processing conditions, in accordance with some embodiments.

In some embodiments, the same processing conditions are used on a sample comprising materials with different elemental concentrations. FIG. 8 illustrates a comparison of two spectrographs. Spectrum 1, 815, corresponds to material with higher concentrations of Element 1, 805, and lower concentrations of Element 2, 810. In contrast, Spectrum 2, 820, corresponds to material with lower concentrations of Element 1, 805, and higher concentrations of Element 2, 810. Monitoring the counts thus provides a way of monitoring the elemental concentrations of a material sample. This information may be used to adjust the processing conditions of the sample based on material composition.

Figure 9:
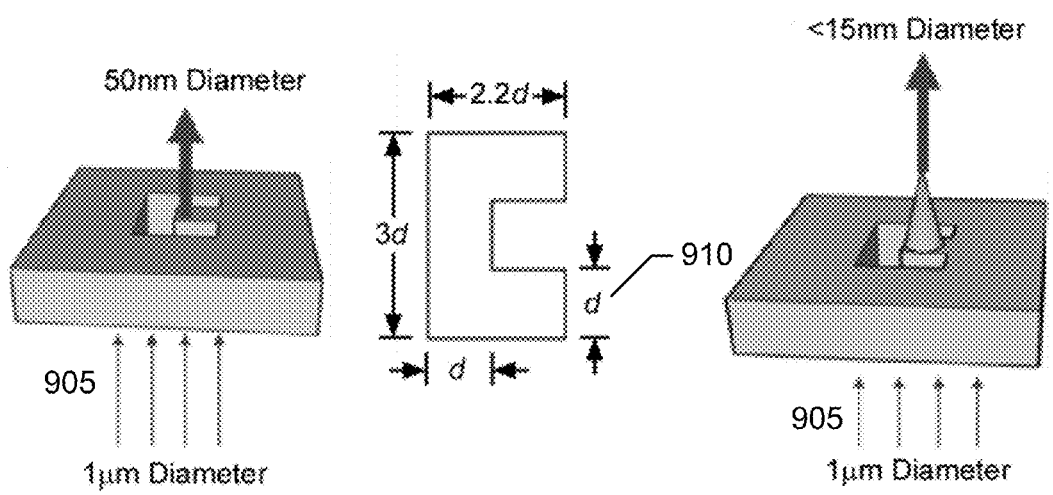
FIG. 9 is a schematic illustration of a nano-aperture, in accordance with some embodiments.

FIG. 9 is a schematic illustration of a nano-aperture, in accordance with some embodiments.

In some embodiments, the nano-aperture comprises two structures having their own functionalities. FIG. 9 illustrates a nano-aperture comprising a C-shaped nano-aperture and a nano-antenna. The C-shaped nano-aperture on the thin gold layer collects the photons from the incoming laser beam 905. The characteristic size of the C-shaped aperture d, 910, is 10-500 nm. The nano-antenna then concentrates the photons to the nano-meter region. In this embodiment, the photons are concentrated to less than 15 nm. The nano-aperture may be fabricated either by Focused Ion Beam (FIB) Milling or by E-beam lithography for large scale integration.

Figure 10:
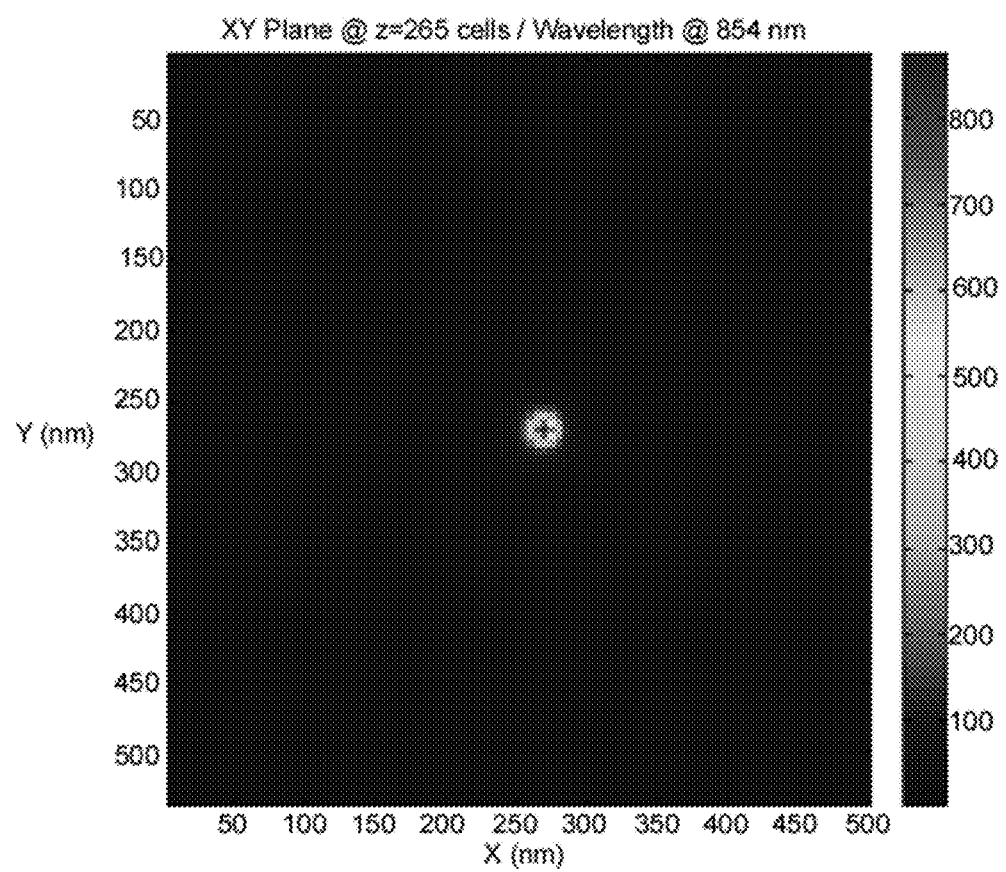
FIG. 10 is a finite-difference time-domain (FDTD) simulation of the intensity field distribution of the laser pulse for the nano-aperture shown in FIG. 9, in accordance with some embodiments.
Figure 11:
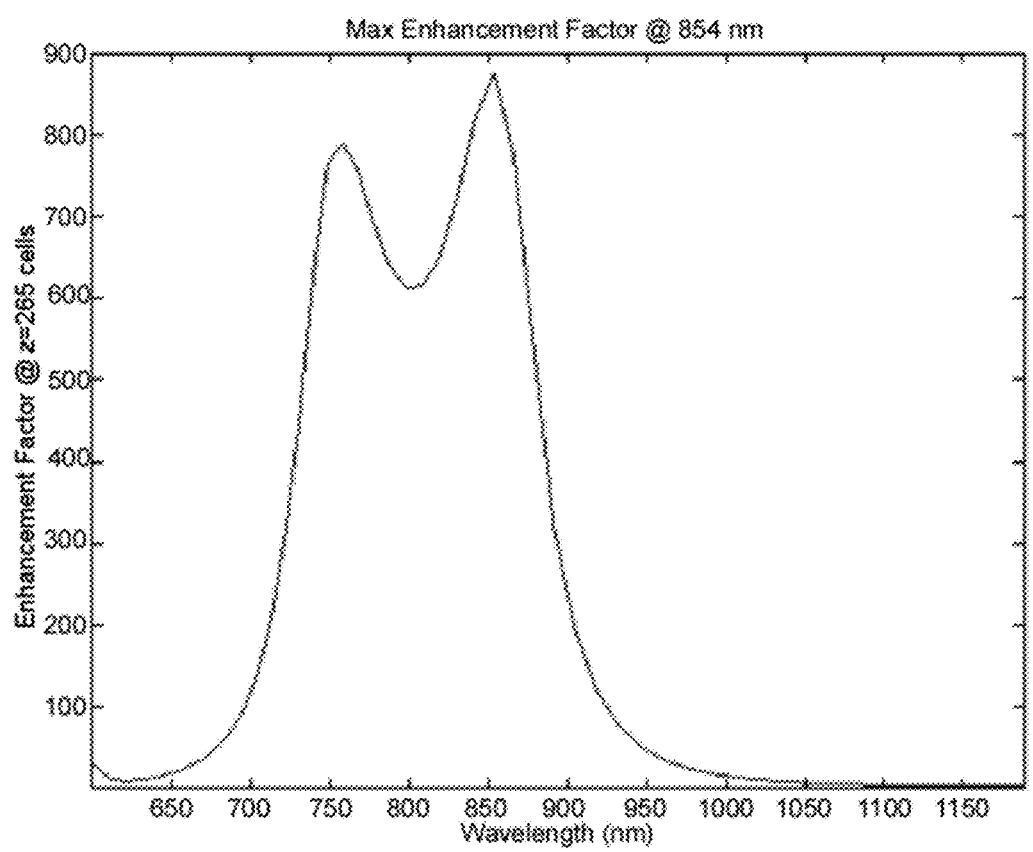
FIG. 11 is a graph illustrating an intensity enhancement of greater than 600 times for the nano-aperture shown in FIG. 9, in accordance with some embodiments.

FIG. 10 is a finite-difference time-domain (FDTD) simulation of the intensity field distribution of the laser pulse and FIG. 11 shows the gain enhancement for the nano-aperture shown in FIG. 9.

In some embodiments, a nano-aperture as illustrated in FIG. 9 is capable of confining the USP laser to less than 15 nm. An FDTD simulation, as shown in FIG. 10, of the nano-aperture illustrated in FIG. 9 shows the intensity field to be confined to less than 15 nm. FIG. 11 shows that the gain is enhanced by greater than 600 for the nano-aperture illustrated in FIG. 9.

Figure 12:
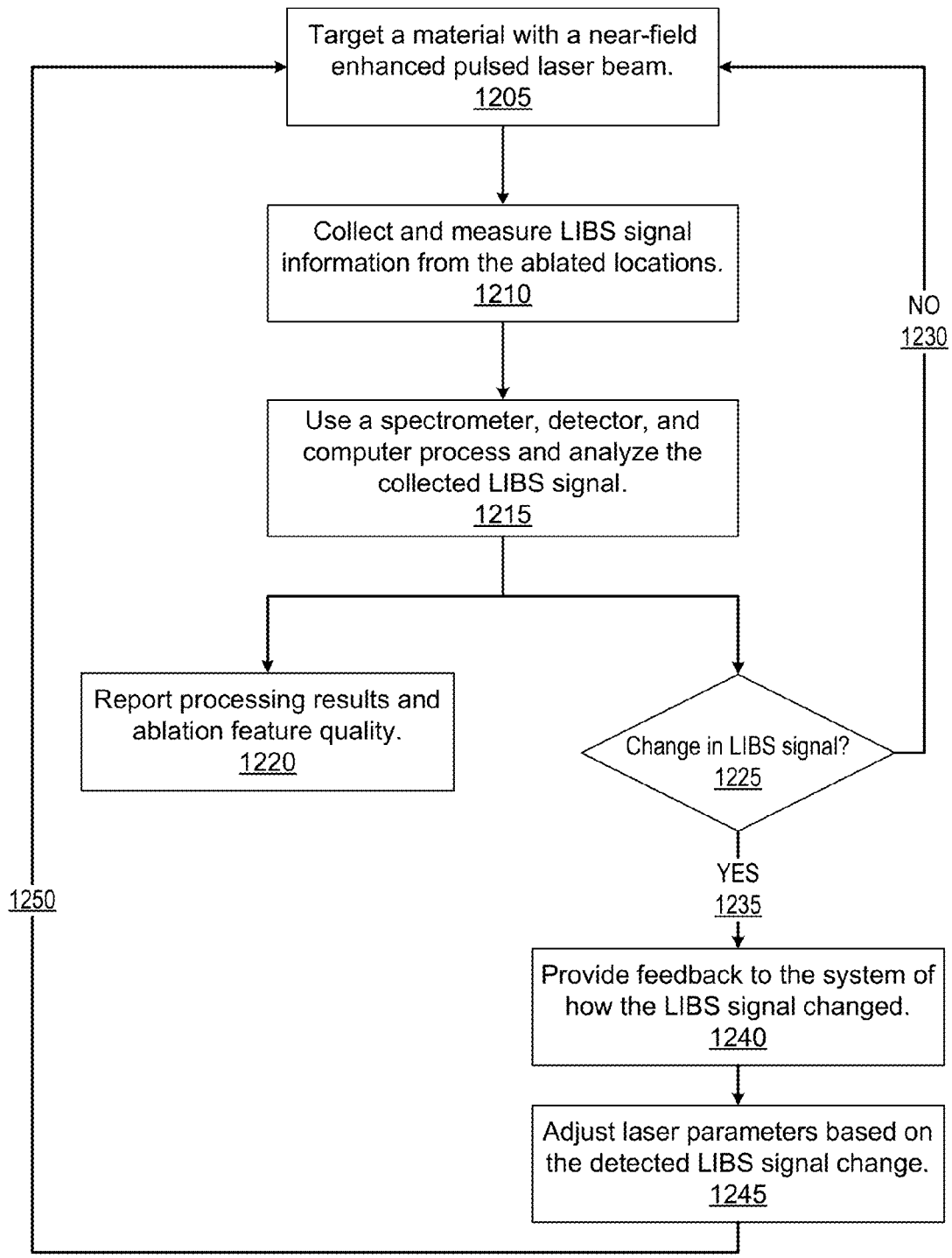
FIG. 12 is a block diagram illustrating a method of near-field material processing with real time feedback and control, in accordance with some embodiments.

FIG. 12 is a block diagram illustrating a method of near-field material processing with real time feedback and control, in accordance with some embodiments.

In some embodiments, a USP fiber laser and a nano-tip or nano-aperture are used to target a material with a near-field enhanced pulsed laser beam 1205. The near-field enhanced pulsed laser beam creates a plume of plasma. The LIBS signal information from the ablated locations is collected and measured by a collecting fiber tip 1210. The collected signal then undergoes spectrum processing, analysis, and diagnostics using a spectrometer, detector, and computer 1215. The processing results and ablation feature quality may be reported 1220. A determination is then made to see if there was any change in the LIBS signal 1225. If a change was not detected 1230, processing returns to step 1205 with the same laser parameters, repeating the ablation, collection, measurement, and analysis. If a change was detected 1235, feedback is provided to the system of how the LIBS signal changed 1240 in order to adjust the laser parameters based on the detected LIBS signal change 1245. Processing then continues 1250 back to step 1205 with the adjusted laser parameters. For example, in some embodiments, when the feedback shows that there is an appearance of one chemical element and disappearance of another element, system control determines that the ablated layer material is changed and so instructs the laser to change the processing parameters (pulse energy, repetition rate and speed) optimized to that specific layer material. In some embodiments, the feedback shows that the relative count numbers of the spectrum spikes are decreasing. The system computer then instructs the laser to increase the pulse energy before repeating the ablation, collection, measurement, and analysis. Accordingly, a technique of end-point detection can be implemented in this way.

Figure 13:
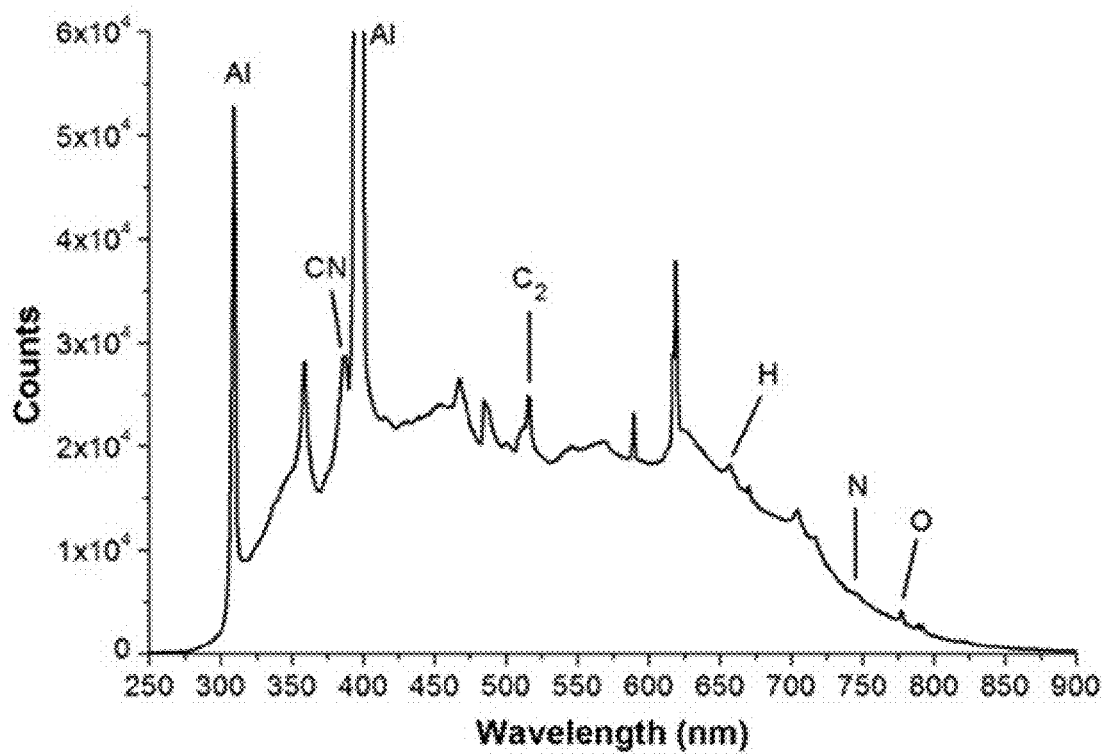
FIG. 13 is a graph illustrating a LIBS signal for TNT on aluminum foil, in accordance with some embodiments.

FIG. 13 is a graph illustrating a LIBS signal for TNT on aluminum foil, in accordance with some embodiments.

In some embodiments, the near-field material processing system may be used for the detection of explosive materials. FIG. 13 shows the fs LIBS signal for TNT on Aluminum foil with line scanning The pulse energy used is 3.0 µJ and the repetition rate is 225 kHz. The scanning speed is 40 mm/s and the total integration time for spectrum collection is 2 s. A significant portion of the laser energy is absorbed by the aluminum foil due to the thin TNT residue thickness. The two strongest peaks in the spectrum are aluminum emission lines from the substrate with wavelengths of 309.28 nm and 396.16 nm (saturated). Emission from the elemental constituents of the explosive include: C (247.86 nm, not shown here due to filter block), H (656.56 nm), N (747.02 nm), and O (777.32 nm). The oxygen peak is a product of three closely spaced transitions of neutral oxygen at wavelengths of 777.19 nm, 777.42 nm, and 777.54 nm. Moreover, molecular emission from CN (388.32 nm) and $C_2$ (516.54 nm) are observed as shown in the FIG. 13, which are important representative peaks for explosive material LIBS signal. The LIBS plasma is a complex system that consists of interactions not only of the laser with the sample, but also the laser with the plasma and the plasmas with the atmosphere. This is a particularly important issue when dealing with organic samples due to the fact that many of the elements that are selected as discriminators are also commonly found in air. For example, most explosive materials predominantly contain carbon, hydrogen, oxygen, and nitrogen. Atmospheric oxygen and nitrogen entrained in the plasma will contribute to the atomic emission from the oxygen and nitrogen from the explosive sample. In addition, if the substrate is an organic material, the carbon and hydrogen will interfere with the atomic emission from the explosive. However, as illustrated in FIG. 13, the LIBS plasma from fs regime has minimized interference and contributions from the atmosphere and the fs laser interaction is better than ns laser interaction to build a stable library for discrimination of organic compounds. Any CN formation from carbon and nitrogen recombination that may occur is not visible above the noise in the air atmosphere for the fs laser regime. Thus, explosive material detection may be realized by using a fs fiber laser with a non-gated, non-intensified detector. Such a system has advantages such as less continuum background, less air entrainment, and less substrate interrogation. This is very beneficial for explosive residue detection from both a cost analysis point of view and a compact size point of view. This commercial fs laser system is more reliable and relatively inexpensive compared with fs solid state lasers. No expensive components (i.e., ICCD & delay generator) are needed and compact fiber laser systems can be used instead of more costly bench top laser systems. This material processing system can be used in extreme environments, such as material processing containing explosive material.

Figure 14:
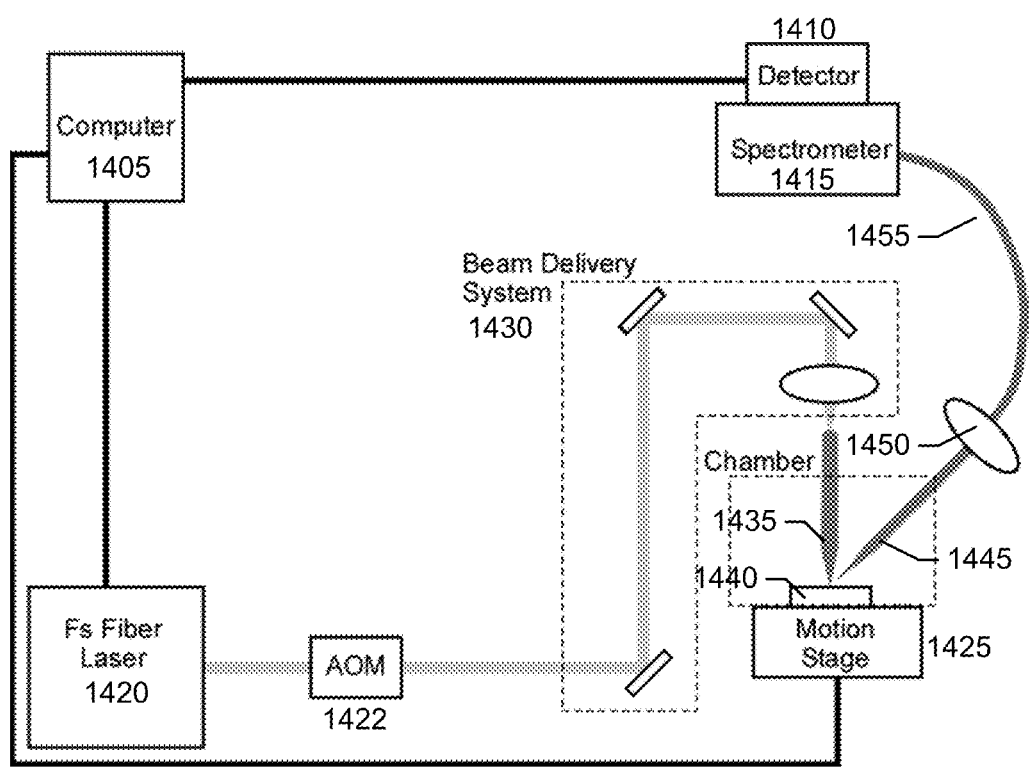
FIG. 14 is a schematic illustration of the near-field material processing system used in FIG. 13, in accordance with some embodiments.

FIG. 14 is a schematic illustration of the near-field material processing system used in FIG. 13, in accordance with some embodiments.

In some embodiments, as illustrated in the spectral graph of FIG. 13, expensive components such as ICCDs and delay generators are not needed. FIG. 14 shows such a system having a computer 1405 interconnected with a detector 1410, a spectrometer 1415, a fs fiber laser 1420, an AOM 1422, and a motion stage 1425. Femtosecond laser pulses are delivered by the beam delivery system 1430 and beam delivery fiber 1435 to create a plasma on the surface of the sample 1440. The plasma plume is collected with a plasma spectrum collection system. The plasma spectrum collection system comprises a tapered optical fiber 1445 that couples, with a coupler 1450, the electromagnetic information from the plasma plume into an optical fiber bundle 1455. The other end of the optical fiber bundle is coupled to the spectrometer 1415.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

The invention claimed is:

1. A system comprising:
   a central processing unit;
   a Ultra-Short Pulsed laser;
   an acousto-optic modulator comprising an input and an output, wherein the USP laser is coupled to the input of the acousto-optic modulator;
   a beam delivery system comprising an input and an output, wherein the output of the acousto-optic modulator is coupled to the input of the beam delivery system;
   a beam delivery fiber comprising an input and an output, wherein the output of the beam delivery system is coupled to the input of the beam delivery fiber and the output of the beam delivery fiber is configured to emit a laser pulse;
   an adjustable stage coupled to the central processing unit and configured to allow positioning of a sample at the output of the beam delivery fiber;
   a plasma spectrum collection system comprising an input and an output, wherein the input of the plasma spectrum collection system is positioned to allow coupling of a plasma electromagnetic radiation generated on the sample by the laser pulse;
   a spectrum analysis unit comprising an input and an output, wherein the output of the plasma spectrum collection is coupled to the input of the spectrum analysis unit; and
   a detector comprising an input and an output, wherein the input of the detector is coupled to the output of the spectrum analysis unit and the output of the detector is coupled to the central processing unit.

2. The system of claim 1, further comprising a nano-aperture coupled to the output of the beam delivery fiber and configured for near-field enhancement of the laser pulse.

3. The system of claim 1, further comprising a delay generator coupled between the central processing unit and both the detector and the USP laser.

4. The system of claim 1, further comprising a camera optically coupled to the beam delivery system and configured to view the sample.

5. The system of claim 1, further comprising a frequency conversion system coupled between the acousto-optic modulator and the beam delivery system.

6. The system of claim 1, wherein the laser pulse has a pulse duration ranging from about 1 fs to about 50 ps.

7. The system of claim 1, wherein the laser pulse has a pulse energy ranging from about 0.001 µJ to about 100 mJ.

8. The system of claim 1, wherein the laser pulse has a single pulse fluence ranging from about 0.001 J/cm$^2$ to about 100 J/cm$^2$.

9. The system of claim 1, wherein the laser pulse has a pulse repetition rate ranging from about 1 kHz to about 100 MHz.

10. A system comprising:
    a central processing unit;
    a Ultra-Short Pulsed laser;
    an acousto-optic modulator comprising an input and an output, wherein the USP laser is coupled to the input of the acousto-optic modulator;
    a beam delivery system comprising an input and an output, wherein the output of the acousto-optic modulator is coupled to the input of the beam delivery system and the output of the beam delivery system is configured to emit a laser pulse;
    an adjustable stage coupled to the central processing unit and configured to allow positioning of a sample at the output of the beam delivery system;
    a plasma spectrum collection system comprising an input and an output, wherein the input of the plasma spectrum collection system is positioned to allow coupling of a plasma electromagnetic radiation generated on the sample by the laser pulse;
    a spectrum analysis unit comprising an input and an output, wherein the output of the plasma spectrum collection is coupled to the input of the spectrum analysis unit; and
    a detector comprising an input and an output, wherein the input of the detector is coupled to the output of the spectrum analysis unit and the output of the detector is coupled to the central processing unit.

11. The system of claim 10, further comprising a nano-tip positioned at the focus of the output of the beam delivery fiber and configured for near-field enhancement of the laser pulse.

12. The system of claim 10, further comprising a delay generator coupled between the central processing unit and both the detector and the USP laser.

13. The system of claim 10, further comprising a camera optically coupled to the beam delivery system and configured to view the sample.

14. The system of claim 10, further comprising a frequency conversion system coupled between the acousto-optic modulator and the beam delivery system.

15. The system of claim 10, wherein the laser pulse has a pulse duration ranging from about 1 fs to about 50 ps.

16. The system of claim 10, wherein the laser pulse has a pulse energy ranging from about 0.001 µJ to about 100 mJ.

17. The system of claim 10, wherein the laser pulse has a single pulse fluence ranging from about 0.001 J/cm$^2$ to about 100 J/cm$^2$.

18. The system of claim 10, wherein the laser pulse has a pulse repetition rate ranging from about 1 kHz to about 100 MHz.

19. A method for real time feedback and control of near-field material processing, the method comprising:
    generating electromagnetic radiation from a Ultra-Short Pulsed laser coupled to a central processing unit;
    coupling the electromagnetic radiation from the USP laser to an input of an acousto-optic modulator;
    coupling the electromagnetic radiation from an output of the acousto-optic modulator to an input of a beam delivery system;
    coupling the electromagnetic radiation from an output of the beam delivery system to an input of a beam delivery fiber;
    using the electromagnetic radiation from an output of the beam delivery fiber to generate a plasma on a target mounted to an adjustable stage coupled to the central processing unit;
    coupling the electromagnetic radiation from the plasma to an input of a plasma spectrum collection system;
    coupling the electromagnetic radiation from an output of the plasma spectrum collection system to an input of a spectrum analysis unit;
    coupling the electromagnetic radiation from an output of the spectrum analysis unit to an input of a detector; and
    coupling an output of the detector to the central processing unit;
    wherein the central processing unit uses the output from the detector as feedback in making adjustments to the USP laser and the adjustable stage.

20. The method of claim 19, wherein the beam delivery fiber comprises a nano-aperture coupled to the output of the beam delivery fiber and is configured for near-field enhancement of the electromagnetic radiation from the output of the beam delivery fiber.

21. The method of claim 19, wherein a delay generator is coupled between the central processing unit and both the detector and the USP laser.

22. The method of claim 19, wherein a camera is optically coupled to the beam delivery system and configured to view the target.

23. The method of claim 19, wherein a frequency conversion system is coupled between the acousto-optic modulator and the beam delivery system.

24. The method of claim 19, wherein the electromagnetic radiation from the output of the beam delivery fiber has a pulse duration ranging from about 1 fs to about 50 ps.

25. The method of claim 19, wherein the electromagnetic radiation from the output of the beam delivery fiber has a pulse energy ranging from about 0.001 µJ to about 100 mJ.

26. The method of claim 19, wherein the electromagnetic radiation from the output of the beam delivery fiber has a single pulse fluence ranging from about 0.001 J/cm$^2$ to about 100 J/cm$^2$.

27. The method of claim 19, wherein the electromagnetic radiation from the output of the beam delivery fiber has a pulse repetition rate ranging from about 1 kHz to about 100 MHz.

28. A method for real time feedback and control of near-field material processing, the method comprising:
   generating electromagnetic radiation from a Ultra-Short Pulsed laser coupled to a central processing unit;
   coupling the electromagnetic radiation from the USP laser to an input of an acousto-optic modulator;
   coupling the electromagnetic radiation from an output of the acousto-optic modulator to an input of a beam delivery system;
   using the electromagnetic radiation from an output of the beam delivery system to generate a plasma on a target mounted to an adjustable stage coupled to the central processing unit;
   coupling the electromagnetic radiation from the plasma to an input of a plasma spectrum collection system;
   coupling the electromagnetic radiation from an output of the plasma spectrum collection system to an input of a spectrum analysis unit;
   coupling the electromagnetic radiation from an output of the spectrum analysis unit to an input of a detector; and
   coupling an output of the detector to the central processing unit;
   wherein the central processing unit uses the output from the detector as feedback in making adjustments to the USP laser and the adjustable stage.

29. The method of claim 28, the method further comprising positioning a nano-tip at the focus of the output of the beam delivery system to provide near-field enhancement of the electromagnetic radiation from the output of the beam delivery system.

30. The method of claim 28, wherein a delay generator is coupled between the central processing unit and both the detector and the USP laser.

31. The method of claim 28, wherein a camera is optically coupled to the beam delivery system and configured to view the target.

32. The method of claim 28, wherein a frequency conversion system is coupled between the acousto-optic modulator and the beam delivery system.

33. The method of claim 28, wherein the electromagnetic radiation from the output of the beam delivery system has a pulse duration ranging from about 1 fs to about 50 ps.

34. The method of claim 28, wherein the electromagnetic radiation from the output of the beam delivery system has a pulse energy ranging from about 0.001 µJ to about 100 mJ.

35. The method of claim 28, wherein the electromagnetic radiation from the output of the beam delivery system has a single pulse fluence ranging from about 0.001 J/cm$^2$ to about 100 J/cm$^2$.

36. The method of claim 28, wherein the electromagnetic radiation from the output of the beam delivery system has a pulse repetition rate ranging from about 1 kHz to about 100 MHz.

\* \* \* \* \*